United States Patent [19]

Maurin

[11] Patent Number: 6,143,307
[45] Date of Patent: *Nov. 7, 2000

[54] COSMETIC COMPOSITION IN THE FORM OF A TRANSPARENT FOAMING GEL

[75] Inventor: Véronique Maurin, Paris, France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/964,148

[22] Filed: Nov. 6, 1997

[30] Foreign Application Priority Data

Nov. 7, 1996 [FR] France ................................. 96 13601

[51] Int. Cl.⁷ ............................... A61K 7/00; A61K 7/06; A61K 7/075
[52] U.S. Cl. .................... 424/401; 424/70.1; 424/70.21; 514/944; 514/945
[58] Field of Search .................................. 424/401, 70.1, 424/70.21; 514/944, 945

[56] References Cited

U.S. PATENT DOCUMENTS

| 4,153,726 | 5/1979 | Borggrefe et al. ...................... 424/313 |
| 4,879,107 | 11/1989 | Vanlerberghe et al. ................... 424/70 |

FOREIGN PATENT DOCUMENTS

| 0 357 561 | 3/1990 | European Pat. Off. . |
| 2 258 833 | 8/1975 | France . |
| 2 151 657 | 7/1985 | United Kingdom . |
| WO 91/07943 | 6/1991 | WIPO . |

OTHER PUBLICATIONS

Derwent Abstracts No. 92–100846 of JP 04–149,112, (May 22, 1992).
English Language Derwent Abtract of EP 0 357 561; Mar. 1990.
Database WPI, Week 9612, Derwent Publications Ltd., London, GB; AN 96–112601; XP 002036849, "Clear gel for hair—consists of water–soluble polymer, polyhydric alcohol and foaming agent", Sep. 1996.
Database WPI, Week 9602, Derwent Publications Ltd., London, GB; AN 96–017105; XO 992936113, "Make–up cleaner having high detergency—contg. polyoxyethylene monoester and maltitol ether", Nov. 1995.

*Primary Examiner*—Shelley A. Dodson
*Assistant Examiner*—Marina Lamm
*Attorney, Agent, or Firm*—Finnegan, Henderson, Farabow, Garrett, and Dunner, LLP

[57] ABSTRACT

Cosmetic compositions in the form of a transparent foaming gel comprising:

(i) at least one alkyl ether carboxylic acid with a fatty chain,
(ii) at least one diol with a fatty chain, and
(iii) water.

24 Claims, No Drawings

COSMETIC COMPOSITION IN THE FORM OF A TRANSPARENT FOAMING GEL

The present invention is directed to a cleaning composition in the form of a transparent foaming aqueous gel based on alkyl ether carboxylic acids with a fatty chain and on fatty diols.

Cleaning the skin is very important for caring for the face and body. It must be as effective as possible because fatty residues, such as excess sebum, residues from the cosmetic products which are used daily and make-up products, in particular water-resistant or "waterproof" products, accumulate in skin folds and at the surface of the skin and can block skin pores and lead to the appearance of spots or blemishes. A poor cleaning quality is often responsible, among other causative factors, for a sallow complexion.

Compositions based on alkaline salts of fatty acids (soaps), often in the form of solid bars, or based on mixtures of these soaps with synthetic surfactants, are conventionally employed for cleaning the skin. While these products are valued for their cleaning properties, their foam and their good rinsability, they are not without disadvantages; in particular, they are supposed to strip the skin, destroying the aqueous/lipid film of the skin, and they leave the skin clean but rough.

Some users blame soap-free cleaning compositions exclusively based on synthetic surfactants for leaving a film on the skin after rinsing, a property which is often associated with poor rinsability. In addition, these compositions are frequently blamed for drying the skin when they are used too frequently. Finally, these compositions, while they can produce a copious foam, do not make it possible to obtain a foam having the fine, dense and close texture which is characteristic of soaps.

In addition, when it is desired to give an aqueous surface-active composition the consistency of a gel, it is usually necessary to incorporate at least one thickening agent in it, such as, for example, a thickening polymer or salts. The incorporation of such additives in aqueous surface-active compositions often has the disadvantage of harming the quality of the foam. In addition, polymeric thickeners can be expensive.

Compositions based on anionic surfactants and on fatty diols are known, for example, from document WO90/0942, the disclosure of which is specifically incorporated by reference herein. These compositions are used for cleaning textiles and use, as anionic surfactants, derivatives from the group of methyl alkyl sulphocarboxylates and alkylbenzenesulphonates. Such compositions do not correspond to the characteristics of the present invention. The teaching of WO90/0942 does not make it possible to prepare compositions corresponding to the characteristics of the present invention, as will be illustrated in the comparative tests discussed below.

The need thus remains for a product for cleaning the skin that has the advantages of a soap in terms of quality of foam and rinsability and that does not have the disadvantages of a soap (dryness, irritation), this product furthermore having a pleasant appearance and a consistency which tends to make it easy to handle.

The subject of the invention is thus a cosmetic composition in the form of a transparent foaming gel comprising at least one alkyl ether carboxylic acid with a fatty chain, at least one diol with a fatty chain, and water.

The compositions according to the invention are characterized (1) by their consistency, which is that of a gel, (2) by their transparency, which confers an attractive appearance on them, and (3) by their ability to form a copious, fine, dense, close and smooth foam.

The texture of the foam of the compositions according to the invention is reminiscent of that of soaps.

In addition, the compositions of the invention possess a high rinsability and they do not leave a film on the skin, properties which make them comparable with conventional soaps.

On the other hand, the compositions according to the invention are incomparably softer and better tolerated than soaps. They leave the skin clean but not dried out.

Finally, these compositions are completely stable during storage.

The word "transparency" in the context of the present invention means that the characters printed on a newspaper page placed behind a transparent glass bottle containing the composition can be distinguished through this bottle.

The alkyl ether carboxylic acid with a fatty chain is advantageously chosen from the products corresponding to the formula (I):

$$R-(O-C_nH_{2n})_p-O-A-COOM \qquad (I)$$

in which:

R represents a saturated or unsaturated, linear or branched $C_8-C_{30}$ alkyl chain, A represents a saturated or unsaturated, linear or branched $C_1-C_6$ alkanediyl radical, M represents a hydrogen atom, an alkali metal or alkaline-earth metal, an ammonium cation or a cation of an organic base, n=2 or 3, and p is an integer ranging from 1 to 40.

Preferably, in the formula (I):

R represents a $C_{10}-C_{22}$ alkyl chain,

A represents a radical chosen from: $-CH_2-$, $-CH_2-CH_2-$ and $-CH_2-CH_2-CH_2-$, M represents a hydrogen atom, n=2, and/or p is an integer ranging from 2 to 30.

More preferably still, in the formula (I):

R represents a $C_{12}-C_{18}$ alkyl chain,

A represents a $-CH_2-$ radical,

M represents a hydrogen atom, n=2, and/or p is an integer ranging from 3 to 20.

Such products are well known to a person skilled in the art. They are, for example, sold by the company Chem Y, under the trade name Akypo RLM.

The diol with a fatty chain is advantageously chosen from organic alcohols containing two hydroxyl groups and a $C_{10}-C_{22}$, preferably $C_{12}-C_{18}$, hydrocarbon chain.

An alkanediol with an unbranched chain is preferably chosen. An alkanediol with a saturated chain is also preferably chosen. Advantageously, it is a 1,2-alkanediol. Mention may be made, among diols with a fatty chain which can be used in the present invention, of: 1,2-decanediol, 1,2-dodecanediol, 1,2-tetradecanediol, 1,2-hexadecanediol, 1,2-octadecanediol and their mixtures.

Such compounds are well known to a person skilled in the art and are commercially available, for example under the tradename Lanette from the company Henkel.

The compositions according to the invention have the consistency of a gel, without it being necessary to incorporate a thickening additive therein. These compositions preferably have a Brookfield viscosity at 25° C. of greater than or equal to 1 Pa·s and, more preferably still, of greater than or equal to 4 Pa·s.

In order to obtain a gel with a satisfactory consistency and which is completely clear, it is preferable to choose amounts by weight of alkyl ether carboxylic acid with a fatty chain [AK] and/or of diol with a fatty chain [AG], with respect to the total weight of the composition, so that they verify the relationship: [AG]/[AK]≦1/3.5, and more preferably still: [AG]/[AK]≦1/4.

Preferably, in order to obtain a composition having the consistency of a gel with a perfectly homogeneous texture, the choice is made of: 1≦[AK]≦35; preferably of: 2≦[AK]≦25; and more preferably still of: 5≦[AK]≦20.

In order to obtain a gel capable of producing a foam which is similar, in its texture, to that of soaps, it is preferable to choose: 0.5≦[AG]; and more preferably still: 1.5≦[AG].

Furthermore, provision may be made for the composition according to the invention to comprise other components, such as, for example:

foaming surfactants, in order to make possible the formation of a more voluminous foam, these foaming agents preferably being chosen from the class of amphoteric surfactants. Reference may be made to the document "Encyclopedia of Chemical Technology, Kirk-Othmer", volume 22, p. 385–392, 3rd edition, 1979, Wiley, the disclosure of which is specifically incorporated by reference herein, where examples of such surfactants are given. The amphoteric surfactants are preferably chosen from alkyl betaines, alkyl sulphobetaines, alkylamidopropyl betaines, alkali metal or alkaline-earth metal alkylcarboxylglycinates, or imidazolines. Mention may be made, among these families of surfactants, of the following examples: dimethyl betaine, coco-betaine, cocoamidopropyl betaine, cocoamidopropyl hydroxysultaine and disodium cocoamphodiacetate.

non-ionic thickeners which are destructive neither to the transparency nor to the harmlessness of the compositions according to the invention and which do not confer film-forming properties thereon; these thickeners can be chosen from:
  a- $C_1$–$C_6$ alkanolamides or $C_8$–$C_{22}$ alkyl ether carboxylic acids;
  b- the addition products of 10 to 300 mol of ethylene oxide or of propylene oxide with partial esters of polyols having 2 to 16 carbon atoms and of fatty acids having 12 to 22 carbon atoms; among this family of products, it is preferable to choose those having a degree of esterification of greater than or equal to 2;
  c- polyoxyethylenated and/or polyoxypropylenated and/or polyglycerolated $C_{12}$–$C_{22}$ fatty alcohols containing from 20 to 500 ethylene oxide and/or propylene oxide and/or glycerol residues,
  d- $C_{12}$–$C_{22}$ fatty esters of polyoxyethylene and/or of polyoxypropylene and/or of polyglycerol, and/or
  e- block polymers of polyethylene glycol and/or of polypropylene glycol.

All these products are commercially available:

$C_1$–$C_6$ alkanolamides of $C_8$–$C_{22}$ alkyl ether carboxylic acids are, for example, sold by the company Henkel under the trademark Comperlan or by the company Chem Y under the trade name Aminol;

addition products of ethylene oxide or of propylene oxide with partial esters of polyols and of fatty acids are, for example, sold by the company BASF under the trademark Cremophor or by the company Amerchol under the trademark Glucamate;

polyoxyethylenated and/or polyoxypropylenated and/or polyglycerolated $C_{12}$–$C_{22}$ fatty alcohols are, for example, sold by the company ICI under the trademark Brij, $C_{12}$–$C_{22}$ fatty esters of polyoxyethylene and/or of polyoxypropylene and/or of polyglycerol are, for example, sold by the company ICI under the trademark Myrj, block polymers of polyethylene glycol and/or of polypropylene glycol are, for example, sold by the company ICI under the trademark Synperonic.

The compositions according to the invention can additionally comprise, without seeing any deterioration in their qualities, in particular their gelled appearance and their foaming power;

cosmetic oils, up to 10%, preferably 3%, by weight with respect to the total weight of the composition; the nature of these oils is not crucial to the implementation of the invention; they can be chosen from:
  vegetable oils, among which may be mentioned sweet almond oil, hazelnut oil, grape seed oil or olive oil;
  mineral oils, for example liquid paraffin, liquid petrolatum and liquid hydrocarbons generally;

oxyethylenated oils, up to 20%, preferably 10%, by weight with respect to the total weight of the composition; for example, mention may be made, within this category, of oxyethylenated (20 EO) sweet almond oil sold by the company Croda under the trademark Crovol A40; oxyethylenated (10 EO) olive oil sold by the company Cosmetochem under the name of: Huile d'olive W [Olive oil W]; or oxyethylenated triglycerides;

colouring agents, pearlescent agents or pigments; mention may be made, among pearlescent agents, of, for example, fatty acids, esters and diesters of glycol, or fatty alcohols; among pigments: guanine derivatives;

antioxidizing agents, such as, for example, sulphites;

preservatives;

fragrances;

screening agents;

hydrophilic or lipophilic active agents: the active agents for the skin can be anti-ageing active agents, anti-wrinkle active agents, moisturizers or humectants, depigmenting active agents, active agents for combating free radicals (radical oxygen species), nutritive active agents, protective active agents, restructuring active agents, firming active agents, slimming active agents, anti-acne active agents, exfoliative active agents, emollient active agents or alternatively active agents for treating skin diseases, such as mycoses, dermatitides, psoriasis, and the like; these active agents are used, depending on their nature, in their usual proportions and, for example, from 0.01% to 10% by weight with respect to the total weight of the composition; mention may more particularly be made, as anti-acne, anti-ageing, anti-wrinkle, moisturizing and exfoliative active agents, of α-hydroxy acids (glycolic, lactic, malic and citric acids and the like).

insoluble fillers: talc, kaolin, polyethylene powder or polyamide particles, such as, for example, those sold under the name "Orgasol" by the Company Atochem, also known under the name (CTFA) of "polyamide 12" or "polyamide 6"; use may also be made, in these compositions, of Nylon powders listed under the CTFA name of "Nylon 12" or "Nylon 6"; such compositions are advantageous in the cleaning of skin for their exfoliative properties.

The compositions according to the invention additionally comprise water. Usually, water is understood to mean pure water. However, all or part of the water used in the compositions according to the invention can optionally be chosen from mineral and/or thermal waters. In general, a mineral water is fit for consumption, which is not always the case with a thermal water. Each of these waters contains, inter alia, dissolved minerals and trace elements. These waters are known to be employed for specific treatment purposes, depending on the specific trace elements and minerals which they contain, such as moisturization and desensitization of the skin or the treatment of certain dermatoses. Mineral or thermal waters will be understood to denote not only natural mineral or thermal waters but also natural mineral or thermal waters enriched in additional mineral and/or trace element constituents, as well as aqueous mineral and/or trace-element solutions prepared from purified water (demineralized or distilled water).

A natural thermal or mineral water used according to the invention can, for example, be chosen from water from Vittel, water from the Vichy basin, water from Uriage, water from La Roche Posay, water from La Bourboule, water from Enghien-les-Bains, water from Saint Gervais-les-Bains, water from Néris-les-Bains, water from Allevard-les-Bains, water from Digne, water from Maizières, water from Neyrac-les-Bains, water from Lons-le-Saunier, water from Eaux-Bonnes, water from Rochefort, water from Saint Christau, water from Fumades, water from Tercis-les-Bains, water from Uriage-les-Bains and water from Avene.

The compositions according to the invention preferably have a pH ranging from 4.5 to 7.5, in order to guarantee that they are completely tolerated by the skin.

The compositions according to the invention can be provided in the form of a cleaning composition for the skin and/or the hair, an exfoliative composition, a make-up removal composition, a scrubbing composition or a moisturizing composition.

Another subject of the present invention is the use of the compositions according to the invention as defined above as, or for the manufacture of, cosmetic and/or dermatological compositions for application to the skin or the hair, in particular for cleaning and/or caring for the skin.

The compositions according to the invention, which are particularly soft, are entirely suited to cleaning and/or caring for sensitive skin.

The examples which follow are intended to illustrate the invention without, however, limiting the scope thereof.

EXAMPLES

In the examples, the names of the products are the INCI names. For each composition, the percentages are given by weight of active material with respect to the total weight of the composition. The viscosity was measured at 25° C. using a Brookfield viscometer for which the rotational speed of the rotor (rotor I) was set at 5 revolutions/min.

In order to illustrate the advantages of the compositions according to the invention, comparative tests were prepared:
Test I (gel according to the invention):

| Laureth-11 carboxylic acid | 20% |
| --- | --- |
| Lauryl glycol | 5% |
| Cocoamidopropyl hydroxysultaine | 3.5% |
| PEG-160 sorbitan triisostearate | 2% |
| PEG-7 glyceryl cocoate | 2% |

-continued

| Glycerol | 1% |
| --- | --- |
| Preservative | q.s. |
| Demineralized water | q.s. for 100% |

Procedure and characteristics: after homogeneous mixing of all the ingredients, a transparent, clear and colourless gel was obtained which had a viscosity of 6 Pa·s and a pH of 5. The [AG]/[AK] ratio was 1/4.

Test II (comparative example):

| Sodium laureth sulphate | 20% |
| --- | --- |
| Lauryl glycol | 5% |
| Cocoamidopropyl hydroxysultaine | 3.5% |
| PEG-160 sorbitan triisostearate | 2% |
| PEG-7 glyceryl cocoate | 2% |
| Glycerol | 1% |
| Preservative | q.s. |
| Demineralized water | q.s. for 100% |

Procedure and characteristics: after homogeneous mixing of all the ingredients, a cloudy liquid was obtained which had a viscosity of 0.36 Pa·s.

This composition was unstable and decomposed into two phases after storage for 24 h at room temperature.

The compositions of Tests I and II were tested by a panel of 18 people, who were asked to determine which of the compositions corresponded best to the characteristics of "copious foam", "fine foam" and "good cleaning quality" and to attribute a grade ranging from 1 to 5 with respect to satisfying each of these criteria (5=criterion satisfied: 1=criterion not satisfied).

Results:

Number of people having chosen each test:

|  | Test I | Test II |
| --- | --- | --- |
| copious foam: | 11 | 7 |
| fine foam: | 8 | 4 |

For the criterion of good cleaning quality, the total of the points attributed to each test was essentially equivalent.

It was thus found that the compositions according to the invention make it possible to obtain a cleaning quality equivalent to a detergent composition according to the comparative examples. On the other hand, the compositions according to the invention make it possible to obtain a more copious and finer foam than the comparative compositions. In addition, these compositions are entirely harmless, in particular they do not dry out and do not irritate the skin, and they do not deposit a film on the skin.

In order to illustrate the invention, the preparation has been carried out of several compositions according to the invention and of comparative examples which emphasize the relevance of the criteria stated above defining the invention. These examples are described in Table 1 below:

examples according to the invention: 1, 2, 3, 7, 8, 9 and 10 examples outside the invention: 4, 5 and 6

TABLE 1

| EXAMPLES | 1 | 2 | 3 | 4 | 5 | 6 | 7 | 8 | 9 | 10 |
|---|---|---|---|---|---|---|---|---|---|---|
| Laureth-11 carboxylic acid | 25 | — | 7.5 | 7.5 | 7.5 | 7.5 | 20 | 20 | 10 | 20 |
| Laureth-5 carboxylic acid | — | 13.5 | 6.75 | 6.75 | 6.5 | 6.75 | — | — | — | — |
| Lauryl glycol | 5 | 3 | 3 | 6 | 4.6 | — | 5 | 5 | 2.5 | 5 |
| Cocoamidopropyl hydroxysultaine | 3.5 | 3.5 | 3.5 | 6 | 6 | 3.5 | 5 | 5 | 2.5 | — |
| PEG-160 sorbitan triisostearate | 2 | 2 | 2 | 2 | 2 | 2 | 2 | 2 | 1 | 2 |
| Demineralized water | q.s. for 100 | q.s. for 100 | q.s. for 100 | q.s. for 100 | q.s. for 100 | q.s. for 100 | q.s. for 100 | q.s. for 100 | q.s. for 100 | q.s. for 100 |
| Stearyl alcohol | — | — | — | — | — | 3 | — | — | — | — |
| Glycol distearate (pearlescent agent) | — | — | — | — | — | — | — | 2 | — | — |
| pH result | 5.5 | 5.7 | 5.1 | 7 | 7 | 7 | 5 | 5.6 | 7.1 | 5 |
| Viscosity (Pa·s) | 22.7 | 11.2 | 7.1 | 8.5 | — | — | 6.0 | 6.2 | 1.9 | 10 |
| [AG]/[AK] | 1/5 | 1/4.5 | 1/4.7 | 1/2.4 | 1/3 | 1/4.7 | 1/4 | 1/4 | 1/4 | 1/4 |
| OBSERVATIONS | clear gel | clear gel | clear gel | unstable opaque gel | unstable opaque gel | unstable liquid with a milky appearance | clear gel | iridescent gel | clear gel | clear gel |

What is claimed is:

1. A cosmetic composition, said composition comprising:
   (i) at least one alkyl ether carboxylic acid with a fatty chain,
   (ii) at least one diol with a fatty chain, and
   (iii) water,
wherein said composition is in the form of a transparent foaming gel, and further wherein the amounts by weight of said at least one alkyl ether carboxylic acid with a fatty chain [AK] and of said at least one diol with a fatty chain [AG], with respect to the total weight of the composition, satisfy the relationship: $[AG]/[AK] \leq 1/3.5$.

2. A composition according to claim 1, wherein said composition has a Brookfield viscosity at 25° C. of greater than or equal to 1 Pa·s.

3. A composition according to claim 2, wherein said viscosity is greater than or equal to 4 Pa·s.

4. A composition according to claim 1, wherein said at least one alkyl ether carboxylic acid with a fatty acid chain is of the formula (I):

$$R-(O-C_nH_{2n})_p-O-A-COOM \quad (I)$$

wherein:
   R represents a saturated or unsaturated, linear or branched $C_8$–$C_{30}$ alky chain,
   A represents a saturated or unsaturated, linear or branched $C_1$–$C_6$ alkanediyl radical,
   M represents hydrogen, an alkali metal, an alkaline-earth metal or a cation of an organic base,
   n is 2 or 3, and
   p is an integer ranging from 1 to 40.

5. A composition according to claim 4, wherein M represents an ammonium cation.

6. A composition according to claim 4, wherein:
   R represents a $C_{10}$–$C_{22}$ alkyl chain,
   A represents a radical —$CH_2$—, —$CH_2$—$CH_2$— or —$CH_2$—$CH_2$—$CH_2$—,
   M represents hydrogen,
   n is 2, and
   p is an integer ranging from 2 to 30.

7. A composition according to claim 6, wherein R represents a $C_{12}$–$C_{18}$ alkyl chain,
   A represents a —$CH_2$— radical,
   M represents hydrogen,
   n is 2, and
   p is an integer ranging from 3 to 20.

8. A composition according to claim 1, wherein said at least one diol with a fatty chain is an organic alcohol containing two hydroxyl functional groups and a $C_{10}$–$C_{22}$ hydrocarbon chain.

9. A composition according to claim 8, wherein said at least one diol with a fatty chain is an organic alcohol containing two hydroxyl functional groups and a $C_{12}$–$C_{18}$ hydrocarbon chain.

10. A composition according to claim 9, wherein said at least one diol with a fatty chain is 1,2-decanediol, 1,2-dodecanediol, 1,2-tetradecanediol, 1,2-hexadecanediol, 1,2-octadecanediol or a mixture thereof.

11. A composition according to claim 1, wherein $[AG]/[AK] \leq 1/4$.

12. A composition according to claim 1, wherein the amounts of said at least one alkyl ether carboxylic acid with a fatty chain [AK] represent from 1% to 35% of the total weight of the composition.

13. A composition according to claim 12, wherein the amounts of said at least one alkyl ether carboxylic acid with a fatty chain [AK] represent from 2% to 25% of the total weight of the composition.

14. A composition according to claim 1, wherein the amounts of said at least one diol with a fatty chain [AG] represent at least 5% of the total weight of the composition.

15. A composition according to claim 1, wherein said composition further comprises at least one additional component, said component being a foaming surfactant; a non-ionic thickener; a cosmetic oil; an oxyethylenated oil; a colouring agent; a pearlescent agent; a pigment; an antioxidizing agent; a preservative; a fragrance; a screening agent; a hydrophilic active agent; a lipophilic active agent; or an insoluble filler.

16. A composition according to claim 15, wherein said foaming surfactants are amphoteric surfactants.

17. A composition according to claim 15, wherein said non-ionic thickener is:
   a $C_1$–$C_6$ alkanolamide or a $C_8$–$C_{22}$ alkyl ether carboxylic acid;
   an addition product of 10 to 300 mol of ethylene oxide with partial esters of polyols having 2 to 16 carbon atoms and fatty acids having 12 to 22 carbon atoms;

an addition product of 10 to 300 mol of propylene oxide with partial esters of polyols having 2 to 16 carbon atoms and fatty acids having 12 to 22 carbon atoms;

a polyoxyethylenated $C_{12}$–$C_{22}$ fatty alcohol, a polyoxypropylenated $C_{12}$–$C_{22}$ fatty alcohol, a polyglycerolated $C_{12}$–$C_{22}$ fatty alcohol, or a mixture thereof, said alcohol containing from 20 to 500 ethylene oxide, propylene oxide, or glycerol residues, or a combination thereof;

a $C_{12}$–$C_{22}$ fatty ester of polyoxyethylene, polyoxypropylene, or polyglycerol, or a combination thereof; or a block polymer of polyethylene glycol, or polypropylene glycol, or a combination thereof.

18. A composition according to claim 17, wherein said addition products have a degree of esterification greater than or equal to 2.

19. A composition according to claim 15, wherein said antioxidizing agents are sulphites.

20. A composition according to claim 1, wherein said composition comprises at least one natural thermal or mineral water wherein said at least one natural thermal or mineral water is water from Vittel, water from the Vichy basin, water from Uriage, water from La Roche Posay, water from La Bourboule, water from Enghien-les-Bains, water from Saint Gervais-les-Bains, water from Néris-les-Bains, water from Allevard-les-Bains, water from Digne, water from Maizières, water from Neyrac-les-Bains, water from Lons-le-Saunier, water from Eaux-Bonnes, water from Rochefort, water from Saint Christau, water from Les Fumades, water from Tercis-les-Bains, water from Uriage-les-Bains or water from Avene.

21. A composition according to claim 1, wherein said composition has a pH ranging from 4.5 to 7.5.

22. A composition according to claim 1, wherein said composition is in the form of a cleaning composition for the skin and/or the hair, an exfoliative composition, a make-up removal composition, a scrubbing composition or a moisturizing composition.

23. A process for cleaning and/or caring for the skin or the hair, said process comprising applying to said skin or hair a composition according to claim 1.

24. A process according to claim 23, wherein said process is for cleaning and/or caring for sensitive skin.

* * * * *